United States Patent [19]

Monceaux et al.

[11] Patent Number: 4,810,647
[45] Date of Patent: Mar. 7, 1989

[54] PROCESS OF PRODUCING ETHANOL AND VARIOUS OTHER BY-PRODUCTS FROM CEREALS

[75] Inventors: Philippe Monceaux, Choisy au Bac; Emile Segard, Compiegne, both of France

[73] Assignee: Valpi, France

[21] Appl. No.: 893,842

[22] Filed: Aug. 6, 1986

[30] Foreign Application Priority Data

Aug. 7, 1985 [FR] France ................... 85 12094

[51] Int. Cl.$^4$ .................. C12P 7/06; A23J 1/12; C07C 29/00; C07K 15/00
[52] U.S. Cl. .................. 435/106; 435/161; 435/162; 435/165
[58] Field of Search ............ 435/161, 93, 95, 106, 435/162, 165

[56] References Cited

U.S. PATENT DOCUMENTS

| 2,698,826 | 1/1955 | Peltzer ................... 435/161 |
| 3,236,740 | 2/1966 | Smith et al. ............. 435/161 |
| 4,035,515 | 2/1977 | Cunningham .......... 435/165 |
| 4,287,304 | 9/1981 | Muller et al. ........... 435/161 |
| 4,361,651 | 11/1982 | Keim ..................... 435/161 |
| 4,421,856 | 12/1983 | Muller et al. ........... 435/165 |
| 4,447,535 | 5/1984 | Zucker et al. .......... 435/162 |
| 4,448,881 | 5/1984 | Muller et al. ........... 435/162 |
| 4,497,896 | 2/1985 | Assarsson et al. ...... 435/165 |

FOREIGN PATENT DOCUMENTS

| 1119538 | 3/1980 | Canada . |
| 1143677 | 3/1983 | Canada . |
| 2442887 | 8/1980 | France . |
| 156921 | 9/1982 | German Democratic Rep. . |
| 220330 | 3/1985 | German Democratic Rep. . |
| 2091293 | 7/1982 | United Kingdom . |

Primary Examiner—Herbert J. Lilling
Attorney, Agent, or Firm—Mason, Fenwick & Lawrence

[57] ABSTRACT

The present invention is related to a process of producing ethanol and gluten from cereals especially from wheat, which comprises the steps if:
 (a) crushing cereals and soaking the thus crushed cereals in water;
 (b) mechanically separating the mixture obtained in step (a) so as to obtain a sediment which contains a major part of the insoluble substances, and a suspension which contains at least 60% of the initially present nitrogen-containing substances;
 (c) subsequently separating the thus produced suspension of step (b), so as to isolate an insoluble fraction containing more than 50% of the initially present proteins and consisting of gluten of said cereals and of a supernatent fraction;
 (d) mixing the sediment obtained in step (b) with said supernatent fraction of step (c) so as to produce a final suspension containing at least 90% of the initial starch;
 (e) submitting the starch contained in said final suspension of step (d) to enzymatic hydrolysis;
 (f) fermenting the suspension as hydrolysed in step (e), while using for such fermenting step a strain of alcoholic yeast;
 (g) separating the fermented suspension of step (f) so as to obtain a supernatent ethanol-containing fraction and a sediment which constitutes a proteinic foodstuff; and
 (h) distilling said supernatent ethanol-containing fraction so as to recover the ethanol contained therein.

In one embodiment of the invention, the hydrolysing step (i.e. step e) is carried out in the form of two successive enzymatic hydrolysis steps.

11 Claims, 1 Drawing Sheet

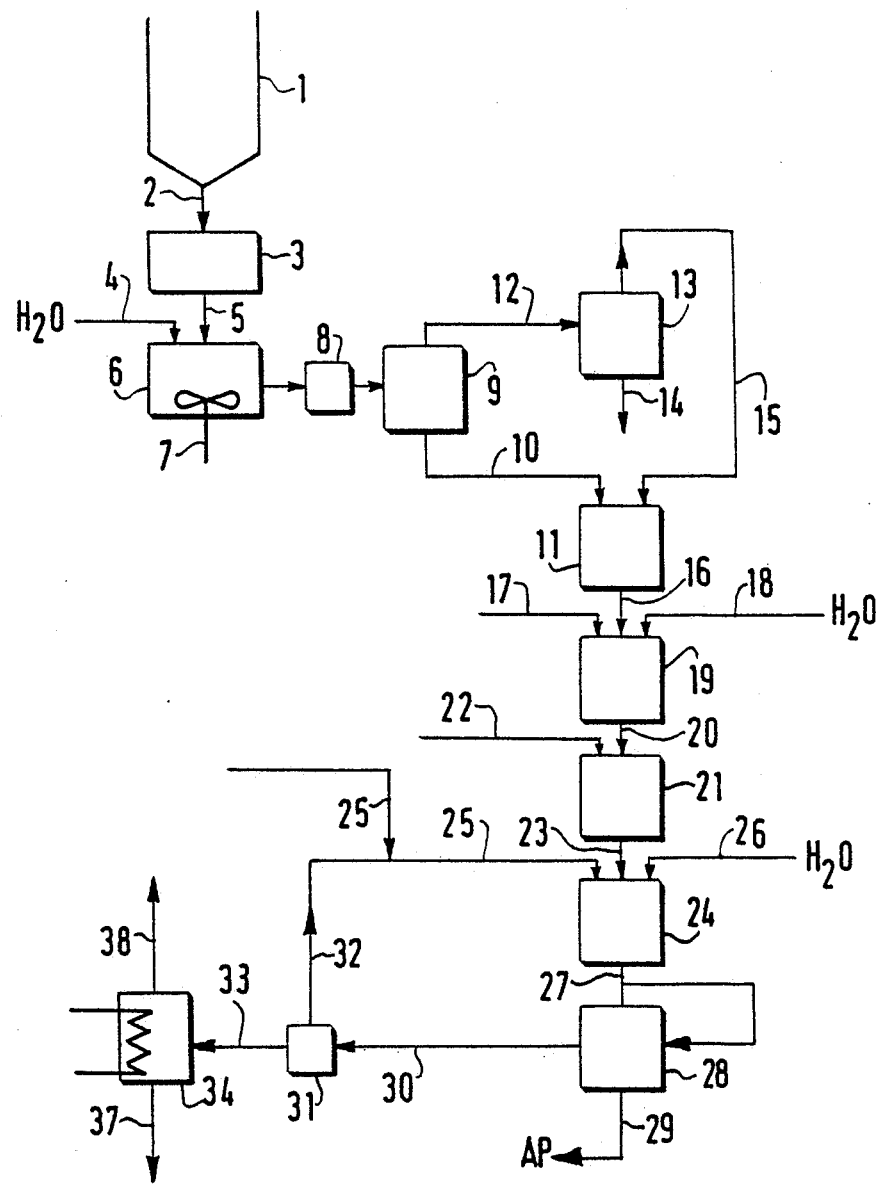

PROCESS OF PRODUCING ETHANOL AND VARIOUS OTHER BY-PRODUCTS FROM CEREALS

FIELD OF THE INVENTION

The present invention is related to a process for producing ethanol and recovering gluten from cereals, especially from wheat.

BACKGROUND OF THE INVENTION

Various methods of producing ethanol from cereals are already known. However, these known methods either involve milling operations, i.e. operations for fractionating the product resulting from crushing or grinding the cereals with a wiev to separating the germs and the bran of the resulting flour, which involves losses of starch and gluten carried off with the germ and bran fraction, whereby the rate of produced ethanol and of the gluten produced is reduced; or said known methods are adapted to avoid such milling and bran separating operations, but then involve crushing of the entire mass without recovering the gluten, while yet allowing an acceptable ethanol production to be achieved.

OBJECT OF THE INVENTION

The present invention is aimed at providing an improved process of treating cereals which overcomes the drawbacks of the known methods and allows, in particular, to obtain gluten (which is a precious product the marketing price of which is comparatively elevated), to obtain ethanol (which can be used for many purposes, and is particularly adapted to be used as a fuel), and which allows also to obtain protein-enriched products (having a protein content higher than 20% of the dry material). This novel process further is meant to exploit a large proportion of the organic substances contained in the water used for the treatment, and to allow the water consumption to be reduced due to considerable recycling and due to a considerable reduction of the load carried by the waste matter.

SUMMARY STATEMENT OF THE INVENTION

With these and other objects in view, the present invention is directed to a process of producing ethanol and gluten from cereals, especially from wheat, which process comprises the steps of:

(a) crushing cereals and soaking the thus crushed cereals in water;

(b) mechanically separating the mixture obtained in step (a) so as to obtain a sediment which contains a major part of the insoluble substances, and a suspension which contains at least 60% of the initially present nitrogen-containing substances;

(c) subsequently separating the thus produced suspension of step (b), so as to isolate an insoluble fraction containing more than 50% of the initially present proteins and consisting of gluten of said cereals and of a supernatent fraction;

(d) mixing the sediment obtained in step (b) with said supernatent fraction of step (c) so as to produce a final suspension containing at least 90% of the initial starch;

(e) submitting the starch contained in said final suspension of step (d) to enzymatic hydrolysis;

(f) fermenting the suspension as hydrolysed in step (e), while using for such fermenting step a strain of alcoholic yeast;

(g) separating the fermented suspension of step (f) so as to obtain a supernatent ethanol-containing fraction and a sediment which constitutes a proteinic foodstuff; and (h) distilling said supernatent ethanol-containing fraction so as to recover the ethanol contained therein.

In one embodiment of the invention, the hydrolysing step (i.e. step (e) is carried out in the form of two successive enzymatic hydrolysis steps.

The first enzymatic hydrolysis step uses the action of amylase with a pH value of about 5.5 to 6.5, at a temperature comprised between 80° and 100° C., during 90 to 150 minutes, while the continuous addition of thermostable amylase and of its activators, such as $Ca^{++}$ ions, is adjusted in such a manner that the initial starch is hydrolysed to form soluble oligosides.

The second enzymatic hydrolysing step comprises the action of amyloglucosidase at pH 4-5, at a temperature of 50° to 70° C., during 12 to 72 hours, the addition of amyloglucosidase being adjusted so as to result in transforming the oligosides into simple sugars.

In accordance with another embodiment of the present invention, the soaking step is carried out under stirring at a temperature lower than or equal to 50° C., the mass ratio of "total crushed material/water effectively present" being comprised between about 0.8 and 2.5.

In still another embodiment of the invention, the mechanical separation of step (b) is carried out in such a manner that the resulting weight distribution corresponds to 40-65% of sediment and 60-35% of suspension, said sediment containing 40-55% of dry substance, while said suspension contains 10-40% of dry substance.

According to yet another embodiment of the invention the subsequent separation of step (c) is carried out in the form of a mechanical separation, using the suspension produced in step (b), at a temperature lower than or equal to 50° C., in such a manner that the supernatent fraction obtained in step (c) contains at least 90% of residual starch, as present in the final suspension.

In one particular embodiment of this invention the supernatent fraction obtained in step (c) is combined with the sediment obtained in step (b), the thus produced mixture then being stirred and adjusted, by addition of water, to a maximum concentration of 25 to 45% of dry material.

In accordance with yet another embodiment of the invention the mixture obtained after the second hydrolysis of step (e) is subjected to an alcoholic fermentation under the action of a convenient strain. Such strain may be, for example, *Saccharomyces Cerevisiae, Saccharomyces Pombe*, etc., said fermentation being carried out at a temperature comprised, for example, between 20° and 45° C.

In still another embodiment of the invention the mixture resulting from the fermentation carried out in step (f) is separated into two phases, to wit: a supernatent ethanol-containing phase (or ethanol-containing effluent) which is to be subjected to an ethanolic distillation, and a proteinic residual phase (or sediment) which constitutes a proteinic foodstuff, said supernatent phase being possibly subjected to a complementary separation step for separating the yeasts which have been carried through, and possibly to a recycling towards the fermentation step (f), while the sediment may possibly be subjected to a washing step for recovering the alcoholic residues which it may contain.

Another object of the invention is to provide an installation which comprises, in succession:

(a) a zone in which the cereals are crushed and in which the thus crushed matter is soaked;

(b) a zone wherein the suspension produced in zone (a) is mechanically separated;

(c) a zone wherein the suspension obtained in zone (b) is separated;

(d) a zone wherein the sediment obtained in zone (c) is mixed;

(e) a zone wherein the starch contained in the suspension produced in zone (d) is hydrolysed;

(f) a zone wherein the suspension hydrolysed in zone (e) is subjected to fermentation;

(g) a zone wherein the fermented suspension obtained in zone (f) is separated into an ethanol-containing supernatent and a sediment constituting a proteinic foodstuff; and (h) a zone wherein said ethanol-containing supernatent is distilled.

The above and other objects, features and advantages of the invention will become more clearly apparent from the following description which refers to the appended drawing and which is given by way of illustration, but not of limitation of the scope of the invention.

BRIEF DESCRIPTION OF THE DRAWING

The single figure of the appended drawing is a simplified block diagram of the process according to the invention.

DETAILED DESCRIPTION OF PREFERRED EMBODIMENTS OF THE INVENTION

The instant process is related to and aimed at transforming wheat into wheat gluten and ethanol. It should be noted however that the invention is in no way limited to the treatment of wheat, but is also applicable to the treatment any other cereals. Similarly, it should be noted that the term "gluten", as used herein designates not only gluten stemming from wheat, but also gluten stemming from any other species of cereals, such as barley, oat, rye, corn, and so forth.

In the installation shown schematically on the appended Figure the cereal matter -which is wheat, in the present embodiment- is initially contained in a silo 1 and is advanced by gravity through a conduit 2 into a crusher 3 wherein the cereals are crushed in such a manner that the resulting crushed cereal matter has a granulometric size (or grain size) of less than 4 mm. The crushed matter is then brought through conduit 5 into a soaking container 6 into which water is fed by means of conduit 4. This soaking container includes stirring means 7. Soaking of the crush cereal material is carried out a temperature of 30° C. and generally during a time period of less than 4 hours, water being fed into said enclosure at a flow rate so selected that the mass ration of crushed matter to water is 1.0. After homogeneization of the suspension in a homogeneizing device said suspension is directed into a mechanical separator 9 constituted by a centrifugal or a so-called hydrocyclonizing device. A sediment containing 50% of dry matter and representing 52% of the material introduced into the mechanical separator 9 is withdrawn from the latter through conduit 10 and is introduced into a mixer 11 which is fed through a conduit 15 with a supernatent fraction stemming from a second separator 13 wherein the supernatent suspension of mechanical separator 9 has been separated into said supernatent fraction flowing through conduit 15 and gluten recovered from separator 13 through conduit 14. The supernatent suspension withdrawn from mechanical separator 13 through conduit 12 contains about 24% of dry matter and constitutes 48% of the mass issuing from separator 9. The gluten thus produced may be subjected to any convenient treatment, such as drying, so as to render it usable under optimum conditions.

In mixer 11 the fractions introduced by conduits 10 and 15 are mixed by mechanical means (not shown), and the resulting mixture is directed through conduit 16 into a first zone of enzymatic hydrolysis 19 which is fed with water, if necessary, through conduit 18, and is fed through conduit 17 with a thermostable amylase. This first hydrolysis is carried out at pH 6,5, at a temperature of 87° C. and during 120 minutes.

For activating the amylase, 200 ppm of a $Ca^{++}$ ion producing substance is added through conduit 18. In this hydrolysing step, it is important that the operating conditions be adjusted so that the starch in presence is hydrolysed to form soluble oligosides.

The mass resulting from this first hydrolysing step is directed through conduit 20 into a second hydrolysing zone 21 for converting into simple sugars, into which zone conduit 22 introduces an amyloglucosidase. This second hydrolysing step is carried out at a temperature of about 62° C. and with a pH value of about 4.7, during 36 hours.

Obviously the above-described two hydrolysing zones can be replaced by a single zone for producing simple sugars, or can be distributed over a plurality of successive zones operating at conveniently stepped respective temperature and pH values.

After hydrolysis the thus hydrolysed mass is directed through conduit 23 into a fermenting device 24 fed with water through conduit 26 and inoculated with *Saccharomyces Cerevisiae* yeast which may be introduced through conduit 25. The temperature in fermenting device 24 is about 30° C. and the dwelling time of the hydrolysed mass in the said device is about 5 hours. The fermented mass is introduced through conduit 27 into a phase separator 28 from the bottom of which a proteinic foodstuff is recovered through conduit 29, while a supernatent ethanol-containing fraction is recovered through conduit 30; this ethanol-containing fraction is then distilled in a distilling device 34 with a view to providing the desired ethanol product. Prior to this distilling step in distilling device 34 said supernatent ethanolic fraction can be subjected to a separation step in a separator 31 wherein the residual yeast possibly carried by the residual fraction since not separated in separator 28 is recovered. This residual yeast is recycled through conduit 32 and feeding conduit 25 into the fermenting device 24, whereas the purified ethanol-containing fraction is directed through conduit 33 into the above-mentioned distilling device.

The ethanol-containing fraction issuing from phase separator 28 is directed immediately into distilling device 34 (which embodiment of the instant process is not shown here), or said fraction, after passing through separator 31 is subjected (as shown in the figure) to distillation in device 34, and the thus obtained ethanol is recovered through conduit 38, while the by-products contained in the raw ethanol-containing fraction are recovered through conduit 37 and possibly admixed again to the proteinic foodstuff withdrawn at 29. This proteinic foodstuff obtained at 29 may then be dried by any convenient method known per se (for example, by the so-called cylinder drying process) so as to provide a flour having a humidity rate of 10% or more, and containing about 23% of proteins with reference to the dry substance. This foodstuff can be used in the form of flour or in the form of pellets for feeding animals.

The output balance of the process is represented in the Table, as based on 1000 kg raw wheat representing 850 kg dry matter, to wit:

N 5.7 ... 100 kg
Starch ... 560 kg
Other substances ... 190 kg

"N 5.7" herein-above means that the protein content equals 5.7 times the total nitrogen.

TABLE

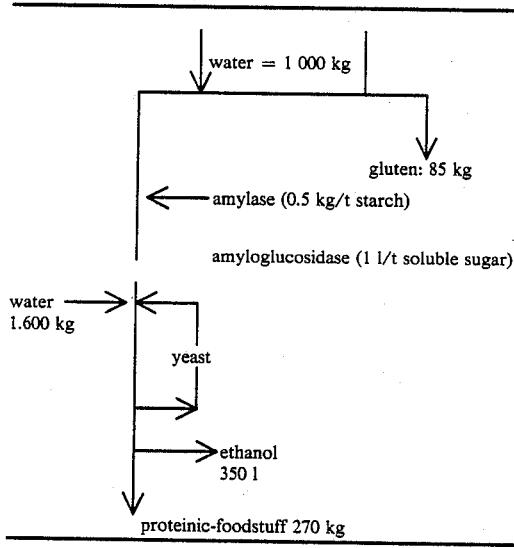

We claim:

1. A process of producing ethanol and gluten from cereals which comprises the steps of:
   (a) crushing cereals and soaking the thus crushed cereals in water;
   (b) mechanically separating the mixture obtained in step (a) so as to obtain a sediment which contains a major part of the insoluble substances, and a suspension;
   (c) subsequently separating the thus produced suspension of step (b), so as to isolate an insoluble fraction containing more than 50% of the initially present proteins and consisting of gluten of said cereals and of a supernatent fraction;
   (d) mixing the sediment obtained in step (b) with said supernatent fraction of step (c) so as to produce a final suspension containing at least 90% of the initial starch;
   (e) submitting the starch contained in said final suspension of step (d) to two successive enzymatic hydrolysis steps;
   (f) fermenting the suspension as hydrolysed in step (e), while using for such fermenting step a strain of alcoholic yeast;
   (g) separating the fermented suspension of step (f) so as to obtain a supernatent ethanol-containing fraction and a sediment which constitutes a proteinic foodstuff; and
   (h) distilling said supernatent ethanol-containing fraction so as to recover the ethanol contained therein.

2. A process according to claim 1, wherein the first one of said two enzymatic hydrolysis steps uses the action of amylase with a pH value of about 5.5 to 6.5, at a temperature comprised between 80° and 100° C., during 90 to 150 minutes, while the continuous addition of thermostable amylase and of its activators is adjusted in such a manner that the initial starch is hydrolysed to form soluble oligosides.

3. A process according to claim 1, wherein the second step of enzymatic hydrolysis uses the action of amyloglucosidase at pH 4-5, at a temperature of 50° to 70° C., during 12 to 72 hours, the addition of amyloglucosidase being adjusted so as to result in transforming the oligosides into simple sugars.

4. A process according to claim 1, wherein the step of soaking said crushed cereals is carried out under stirring at a temperature lower than or equal to 50° C., the mass ratio of "total crushed material/water effectively present" being comprised between about 0.8 and 2.5.

5. A process according to claim 1, wherein said mechanical separation step (b) is carried out in such a manner that the resulting weight distribution corresponds to 40-65% of sediment and 60-35% of suspension, said sediment containing 40-55% of dry substance, while said suspension contains 10-40% of dry substance.

6. A process according to claim 1, wherein said subsequent separation of step (c) is carried out in the form of a mechanical separation, using the suspension produced in step (b), at a temperature lower than or equal to 50° C., in such a manner that the supernatent fraction obtained in step (c) contains at least 90% of residual starch, as present in the final suspension.

7. A process according to claim 1, wherein the supernatent fraction obtained in step (c) is combined with the sediment obtained in step (b), the thus produced mixture then being stirred and adjusted, by addition of water, to a maximum concentration of 25 to 45% of dry material.

8. A process according to claim 1, wherein the mixture obtained after the second hydrolysis of step (e) is subjected to an alcoholic fermentation under the action of a convenient strain.

9. A process according to claim 8, wherein said strain is selected from *Saccharomyces Cerevisiae Saccharomyces Pombe*, said fermentation being carried out at a temperature between 20° and 45° C.

10. A process according to claim 1, wherein the mixture resulting from the fermentation step (f) is separated into two phases, to wit: a supernatent ethanol-containing phase or ethanolic effluent adapted to be subjected to ethanol distillation, and a residual phase comprising a proteinic sediment which constitutes a proteinic foodstuff.

11. A process according to claim 10, wherein said supernatent phase is subjected to a supplementary step of separating any yeast carried by said phase, and of recycling such separated yeast into said step (f) of fermentation.

* * * * *